(12) United States Patent
Fulmer et al.

(10) Patent No.: US 6,465,695 B1
(45) Date of Patent: Oct. 15, 2002

(54) METHOD AND SYSTEM FOR MANUFACTURING CUMENE HYDROPEROXIDE

(75) Inventors: John William Fulmer; Eugene Edward Scott, both of Mt. Vernon; William Dale Kight, Poseyville, all of IN (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/916,775

(22) Filed: Jul. 27, 2001

(51) Int. Cl.[7] ............................................. C07C 409/02
(52) U.S. Cl. ........................ 568/571; 568/568; 568/569
(58) Field of Search ............................. 568/568, 569, 568/571

(56) References Cited

U.S. PATENT DOCUMENTS

| | | | |
|---|---|---|---|
| 2,663,740 A | * 12/1953 | Calhoun et al. | |
| 2,897,239 A | * 7/1959 | Rovelli | 568/577 |
| 3,187,055 A | 6/1965 | Armstrong et al. | 260/610 |
| 3,523,977 A | 8/1970 | Reni et al. | 260/610 |
| 3,907,901 A | 9/1975 | Feder et al. | 260/610 |
| 3,933,921 A | 1/1976 | Suda et al. | 260/610 |
| 4,329,514 A | * 5/1982 | van der Weijst et al. | 568/577 |
| 5,120,902 A | 6/1992 | Tagamolila et al. | 585/836 |
| 5,196,598 A | * 3/1993 | Iwane et al. | 568/575 |
| 5,512,175 A | 4/1996 | Saito et al. | 210/299 |
| 5,767,322 A | 6/1998 | Zakoshansky et al. | 568/571 |
| 5,908,962 A | 6/1999 | Zakoshansky et al. | 568/571 |
| 6,077,977 A | * 6/2000 | Gopinathan et al. | 568/571 |

OTHER PUBLICATIONS

CA:135:305480 abs of RU 2146670 Mar. 2000.*

* cited by examiner

Primary Examiner—Jean F. Vollano

(57) ABSTRACT

A method for manufacturing cumene hydroperoxide comprises reacting cumene and oxygen in the presence of a water phase comprising aqueous ammonia, and in the absence of an additive comprising an alkali or alkaline earth metal, to form cumene hydroperoxide. A system for producing cumene hydroperoxide comprises a cumene feed in fluid communication with a reactor having a cumene hydroperoxide oxidate outlet; an oxygen feed in fluid communication with the reactor; and an ammonia feed in fluid communication with the cumene feed and/or the reactor, wherein the cumene feed, the oxygen feed, the ammonia feed, and the reactor are free of an additive comprising an alkali or alkaline earth metal.

15 Claims, 2 Drawing Sheets

METHOD AND SYSTEM FOR MANUFACTURING CUMENE HYDROPEROXIDE

BACKGROUND OF THE INVENTION

This disclosure relates to methods for cumene oxidation, and in particular to methods and systems for manufacturing cumene hydroperoxide.

Free radical cumene oxidation reactions are well known. They can be conducted in the presence of a water phase, the so-called "heterogeneous wet oxidation" method, or in the absence of a water phase, the "dry oxidation" method. The heterogeneous wet oxidation method is generally preferred, as the presence of water provides improved safety and control of the exothermic reaction, and also requires less capital investment.

Commercially, wet cumene oxidation is conducted by a continuous process using a cascade of at least two gas-sparged reactors, typically three to six, with a variable temperature profile. The main oxidation reaction products are cumene hydroperoxide (CHP, the desired product, which is often used to produce phenol and acetone), along with dimethylbenzyl alcohol and acetophenone. In addition, trace amounts of acidic byproducts, such as formic acid, acetic acid, and phenol, are also produced. These acidic byproducts may inhibit the oxidation reaction, resulting in a decrease in both rate and yield, as well as negatively affecting CHP selectivity. To prevent this, U.S. Pat. Nos. 3,187,055; 3,523,977; 3,687,055; and 3,907,901 variously teach that alkali metal bases, such as sodium hydroxide (NaOH), and bicarbonate salts of alkali metals, such as sodium carbonate ($Na_2CO_3$), can be used as additives to remove the trace acid impurities. The use of a dibasic salt such as sodium carbonate is known to be additionally effective due to its ability to buffer the pH of the mixture and prevent large pH variations. Strongly basic NaOH is generally not preferred due to its tendency to form a water-soluble salt with the product CBP, resulting in loss of the CHP-salt into the oxidate aqueous purge streams, thereby decreasing yields.

The alkali additives are usually added to the reactors as aqueous solutions, whereupon two immiscible phases form. The strong bubbling action from an air stream provides contact and mixing of the two mutually insoluble phases into a partially emulsified mixture. Intimate mixing of the two immiscible phases is critical to obtaining efficient neutralization of the organic acids present in the cumene-CHP organic phase, and special static mixers, as disclosed in U.S. Pat. No. 3,933,921, and counter-current extractors, as disclosed in U.S. Pat. No. 5,120,902, have been employed in the art to aid in their contacting. However, even with these devices the neutralization process is only partially effective because the effectiveness and degree of organic acid neutralization is highly dependent on physical mass transfer limitations between the two contacting, immiscible phases. As a result, the pH of the oxidate reaction mixture may not be well controlled, which results in reduced oxidation reaction selectivity and an increased potential for equipment corrosion.

In U.S. Pat. Nos. 5,767,322 and 5,908,962, an alternative cumene wet oxidation process is described wherein $Na_2CO_3$ and ammonia ($NH_3$) are simultaneously added to the reactors to form a mixed alkaline salt, $NH_4NaCO_3$. Free ammonia is not present since ammonia reacts immediately with the by-product $NaHCO_3$. This mixed alkaline salt, although not truly soluble in the organic oxidate phase, appears to provide improved mass transfer between the two immiscible phases and more effectively neutralizes the undesirable organic acids than $Na_2CO_3$ alone. However, in order to be effective the process disclosed in U.S. Pat. No. 5,908,962 must split the cascade of oxidation reactors into two parallel trains, and must employ a special water stream flow that is counter-current to the cumene feed stream. In practice it has been found that the $Na_2CO_3$, which is a strong base, must be added in very precisely controlled amounts in order to prevent the pH from varying widely, i.e., over 3 to 4 pH units. In addition this process requires the purchase of two alkaline agents and the installation of a complex piping arrangement to manage the myriad of recycle streams. Thus this complicated cumene oxidation system design requires high investment in equipment, labor, and costs.

In addition, in all of the above-mentioned wet oxidation processes, small amounts of the inorganic alkali or alkaline earth metal salts remain entrained within the product CHP-cumene oxidate organic stream, and these salts pass forward into the downstream process steps where they deposit on and foul various pieces of equipment. This problem is particularly troublesome downstream where the distillation column heat exchangers and reboilers foul with regularity while concentrating CHP. This salt fouling reduces heat transfer ability, increases steam consumption, and makes the separations ineffective. Periodic cleaning of these fouled heat exchangers is required, which mandates plant shut down and thus lost production. Such production losses are quite costly in terms of time, labor, associated monetary expenditures, and need to be avoided if at all possible. Installation of coalescer units after cumene oxidation and prior to concentrating the CHP, to filter out and remove the entrained inorganic salts, is disclosed in U.S. Pat. No. 5,512,175. Although this method can be effective, the coalescer units are very large and their purchase and installation requires a high investment cost. The special carbon-fiber coalescer filter elements used inside these units must be replaced on an annual basis, which is also quite costly.

Accordingly there remains a need in the art for a cost effective method and system for manufacturing cumene hydroperoxide that overcomes the drawbacks and disadvantages of the above-identified methods.

BRIEF SUMMARY OF THE INVENTION

The above-mentioned drawbacks and disadvantages are overcome or alleviated by a method and system for manufacturing cumene hydroperoxide, comprising reacting cumene and oxygen in the presence of ammonia or aqueous ammonia, and in the absence of an additive comprising an alkali or alkaline earth metal, to form cumene hydroperoxide.

The system comprises means for producing cumene hydroperoxide from cumene and oxygen in the presence of aqueous ammonia, and in the absence of an additive comprising an alkali or alkaline earth metal.

Another embodiment of a system for cumene oxidation, equally applicable for either the wet or dry mode of operation, comprises a cumene feed in fluid communication with a reactor having a cumene hydroperoxide oxidate outlet; an oxygen feed in fluid communication with the reactor; and an ammonia feed in fluid communication with the cumene feed and/or the reactor, wherein the cumene feed, the oxygen feed, the ammonia feed, and the reactor are free of an additive comprising an alkali or alkaline earth metal. A distillation apparatus may be serially connected with the cumene hydroperoxide oxidate outlet.

BRIEF DESCRIPTION OF THE DRAWING

Referring now to the Figures, which are merely illustrative, wherein the like elements are numbered alike.

DETAILED DESCRIPTION OF THE INVENTION

The inventors hereof have discovered that ammonia, even in the absence of alkali and alkaline earth metal salts or bases, is a very effective neutralizing agent for cumene oxidation. This result is particularly surprising because one of ordinary skill in the art would not expect that ammonia, which is weaker base and not dibasic (and therefore has little or no buffering ability) nonetheless leads to results superior to the stronger, dibasic additives of the prior art. Accordingly, the drawbacks of using the prior art alkali and alkaline earth metal salts or bases, such as sodium carbonate, sodium hydroxide, calcium carbonate, and the like are avoided or prevented by substituting ammonia alone.

An efficient method and system for commercial production of cumene hydroperoxide comprises reaction of cumene with oxygen in the presence of ammonia, but in the absence of additives which must be subsequently purified, or which contribute to the fouling of equipment, in particular additives comprising alkali or alkaline earth metals. "Alkali or alkaline earth metals" means compounds from Group IA or IIA of the periodic table, and additives comprising these metals includes the corresponding hydroxides, hydrates, or salts, e.g., carbonates, phosphates, and the like.

In practice, either the wet or dry cumene oxidation method may be used to advantage with this invention. The wet method is preferred, and accordingly comprises reaction of cumene with oxygen in the presence of an aqueous phase. The ammonia may be introduced separately into a cumene feed, an aqueous feed, or with an oxygen feed. Likewise, any of the various oxidate recycle streams in the system containing undesirable organic acids can be beneficially treated with ammonia external to the main oxidation reactors and prior to their re-introduction into the reactors. Preferably, an aqueous ammonia solution, i.e., ammonium hydroxide ($NH_4OH$) is used.

Figure 1:
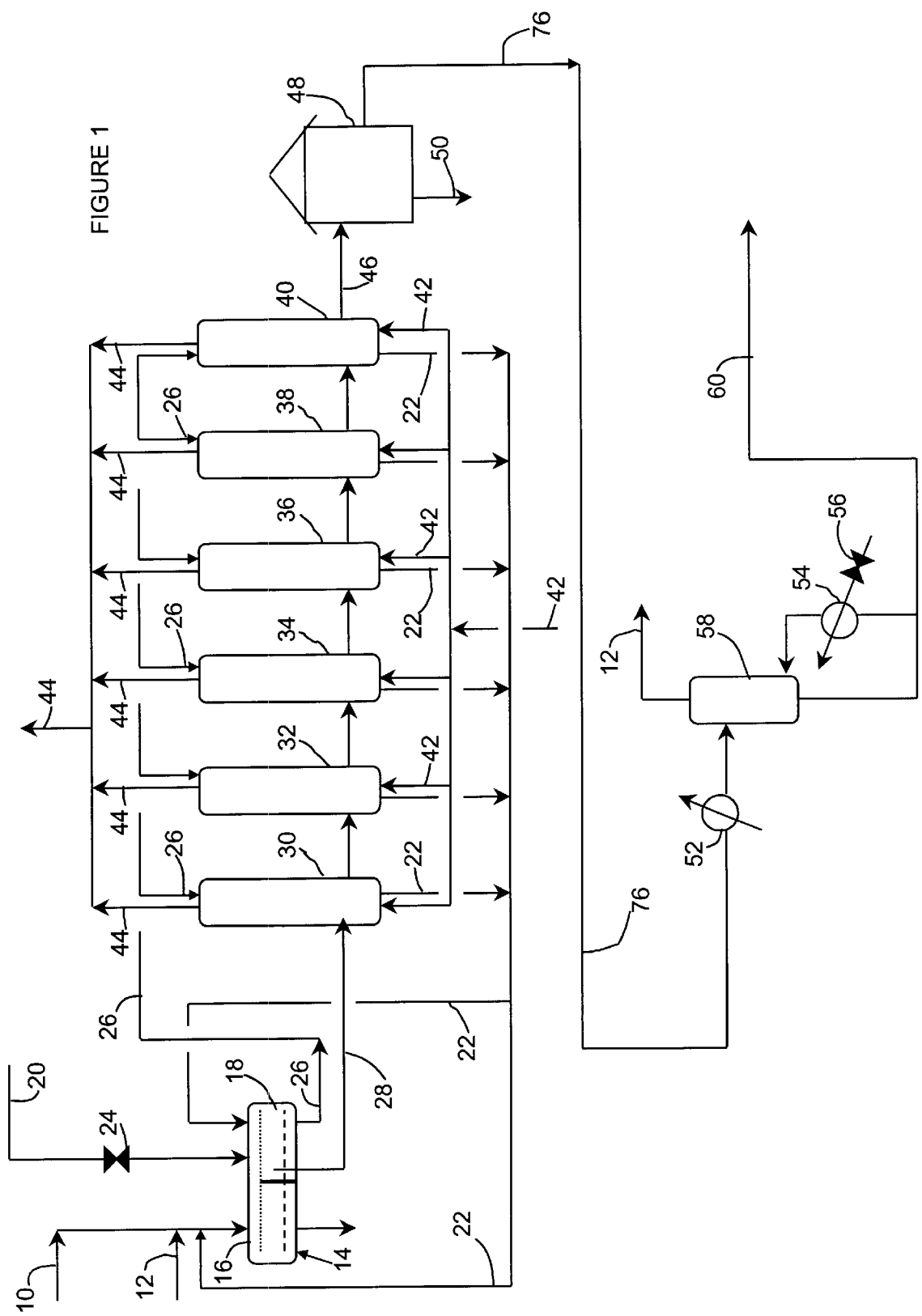
FIG. 1 is a schematic flow diagram illustrating an exemplary embodiment of a method and system for manufacturing cumene hydroperoxide using ammonia.

FIG. 1 illustrates a flow chart showing in detail one embodiment of the method and system for manufacturing cumene hydroperoxide. A cumene feed 10, which may be for example pure cumene, is optionally mixed with a portion of a recycled cumene oxidate stream 12, and enters a settler vessel 14 having a purge compartment 16 and a mixing compartment 18. An ammonia feed stream 20, preferably a dilute aqueous ammonia solution, is optionally mixed with a recycled ammonia stream 22, and is also fed to settler vessel 14, and mixed with the cumene feed. The amount of ammonia entering settler vessel 14 may be controlled using a flow control device 24, e.g., a valve, that is actuated either manually or by an operator via an electronic interface (not shown), and may be optionally monitored using a sensor such as a pressure sensor, an output sensor, a flow rate sensor, a mass flow sensor, or the like. The settler vessel 14 can be charged with an amount of aqueous ammonia effective to maintain the pH of oxidate mixture(s) as described below at greater than or equal to about 5, preferably greater than or equal to about 7; and at a pH less than or equal to about 10, and preferably less than or equal to about 8.

Where aqueous ammonia is used, the mixture may be allowed to settle, forming two distinct phases, a bottom aqueous ammonia phase 26 and a top cumene organic phase 28. The aqueous phase contains the aqueous ammonia solution, and may contain neutralized acid inhibitors from the optional recycled ammonia stream 22, while the organic phase includes the cumene, and may contain organic reaction by-products and other organic components from the optional recycle cumene stream 14.

Aqueous ammonia phase 26 is then fed into reactor 30 (preferably into the top as shown). Aqueous ammonia phase 26 may also be split and fed into sequential reactors 32, 34, 36, 38, and 40. Cumene organic phase 28 is fed into reactor 30 (preferably from the bottom as shown). Suitable reactors are known in the art, and the system preferably comprise three or more reactors, most preferably 3 to 6 reactors, serially disposed in fluid communication with reactor 30. More particularly, the cumene oxidation reaction is carried out in a continuous fashion using a cascade of air-sparged reactors 30, 32, 34, 36, 38, and 40.

Inside each reactor 30, 32, 34, 36, 38, 40 an incoming oxygen feed 42 mixes, preferably turbulently mixes, the two phase streams 26, 28 together. Oxygen feed 42, preferably an air stream containing about 15 to about 25 volume percent (vol. %) oxygen, preferably about 18 to about 22 vol. % oxygen, most preferably 21 vol. % oxygen, is introduced or fed into the bottom portion of each reactor 30, 32, 34, 36, 38 and 40. The oxygen reacts with the cumene to form cumene hydroperoxide and reaction byproducts ("the cumene oxidate").

Each reactor 30, 32, 34, 36, 38, 40 can be maintained at a lower temperature of about 160 degrees Fahrenheit (° F.), preferably 170° F., most preferably 180° F., to an upper temperature of about 240° F., preferably about 230° F., most preferably 220° F., or a temperature range of about 180° F. to about 220° F., and at a lower pressure of about 50 pounds per square inch gauge (psig), preferably 60 psig, most preferably 70 psig, to an upper pressure of about 80 psig, preferably about 90 psig, most preferably 100 psig, or a pressure range of about 70 psig to about 100 psig. The pH is monitored and controlled for each reactor 30, 32, 34, 36, 38 and 40, and may be used to determine the amount of ammonia introduced by feeds 20 and/or 22. The pH of the reaction mixture within each reactor is preferably maintained between about 5 to about 10, preferably between about 6 to about 9, and most preferably between about 7 to about 8.

As oxygen feed 42 rises within each reactor 30, 32, 34, 36, 38, 40, the volume percent oxygen decreases and becomes depleted such that a spent oxygen feed 44 typically containing about 2 to about 10 vol. % oxygen, preferably about 3 to about 8 vol. % oxygen, most preferably about 4 to about 6 vol. % oxygen, is emitted from the top of each reactor 30, 32, 34, 36, 38, 40. Where an aqueous phase is present, the higher density aqueous phase falls to the bottom of the reactors and may be drawn off continuously as a recycled aqueous ammonia stream 22.

At least a portion of the cumene oxidate 62, preferably the entirety of the oxidate 62, is removed and fed into a base portion of each sequential reactor 32, 34, 36, 38 and 40. As the organic phase stream 28 passes through reactors 30, 32, 34, 36, 38, 40 serially disposed in fluid communication, the concentration of cumene hydroperoxide generally increases. The cumene hydroperoxide make profile (i.e., cumene hydroperoxide concentration) in the cascade of reactors 30, 32, 34, 36, 38, 40 can vary. For example, reactor 30 can have about 5 to about 6 weight percent (wt. %) cumene hydroperoxide, while reactor 40 can have about 20 to about 30 wt. % cumene hydroperoxide, or more.

After reaction in final reactor 40, an oxidate product stream 46, typically comprising about 20 to about 30 wt. % cumene hydroperoxide, may be fed into a discharge vessel 48, e.g., a storage tank, so that any remaining aqueous phase may settle and be drawn off as discharge 50. The discharge vessel 48 is preferably serially disposed in fluid communication with and after the last reactor. The separated oxidate product stream 76 is then introduced or fed forward, i.e., downstream, from discharge vessel 48 for further purification, for example by distillation.

The distillation apparatus is serially disposed in fluid communication with and after the storage discharge 48. The distillation apparatus can include but is not limited to standard distillation equipment known in the art as well as one or more distillation components selected from the group consisting of a vacuum distillation apparatus, a distillation column heat exchanger, a reboiler, a shell-and-tube heat exchanger vaporizer, and combinations comprising at least one of the foregoing distillation components. Separated oxidate product stream 76 is preferably subjected to a series of vacuum distillations, e.g., 1 to 3 distillation stages to remove cumene and other by-products, wherein separated oxidate product stream 76 is concentrated to about 80 to about 83 wt. % cumene hydroperoxide.

For purposes of illustration, and not to be interpreted as limiting, FIG. 1 illustrates only one distillation step. The product stream 46 may be concentrated using distillation components such as first and second vaporizing apparatus 52, 54, e.g., a shell-and-tube heat exchanger vaporizer and a primary reboiler, respectively, which employ low pressure steam as a heating medium. The first vaporizing apparatus 52 is serially disposed in fluid communication with and after the storage discharge 48. Steam flow demand to the second vaporizing apparatus 54 and the apparatus temperature can be controlled by a flow control device 56, e.g., a valve actuated either manually or by an operator via an electronic interface (not shown), and optionally a sensor selected from the group consisting of a pressure sensor, an output sensor, a flow rate sensor, a mass flow sensor, and combinations comprising at least one of the foregoing sensors. Separated oxidate product stream 76 is continuously fed from first vaporization apparatus 52 through one or more distillation components, e.g., distillation column 58, preferably three or more distillation components, preferably three distillation columns, and exits into second vaporization apparatus 54. The distillation column 58 is preferably serially disposed in fluid communication between the first vaporizing apparatus 52 and second vaporizing apparatus 54. The second vaporization apparatus 54 reintroduces at least a portion of product stream 46 into the distillation components 58 to further concentrate and improve the yield of the resulting concentrated product stream 60. Concentrated product stream 60 is drawn from the distillation column 58, preferably from at least a portion of the base of distillation column 58. Optionally, a recycled cumene stream 12 (not shown) may be removed from at least a portion of the top of the distillation column 58 to be combined with a cumene stream 10 and recycled for reuse in reactors 30, 32, 34, 36, 38 and 40.

While the above description represents a preferred embodiment, other systems and configurations may also be used. For example, one or more of cumene, water, and ammonia may be fed directly into reactor 30. Addition of aqueous ammonia to one or more returning oxidate or aqueous ammonia recycle streams may also be used. It is also contemplated that anhydrous ammonia, i.e., ammonia gas ($NH_3$) may be contained in an incoming air feed stream entering each reactor, separately from or together with the oxygen feed stream. This invention applies equally to both wet and dry modes of cumene oxidation and can also be applied to advantage in analogous free radical air oxidation processes of other alkylaromatic compounds, for example air oxidation of ethylbenzene, sec-butylbenzene and di-isopropylbenzene. The produced cumene hydroperoxide may be used in a number of applications, including the acid-catalyzed cleavage of cumene hydroperoxide to phenol and acetone.

The invention is further illustrated by the following non-limiting examples.

EXAMPLES

Comparative Example 1

Figure 2:
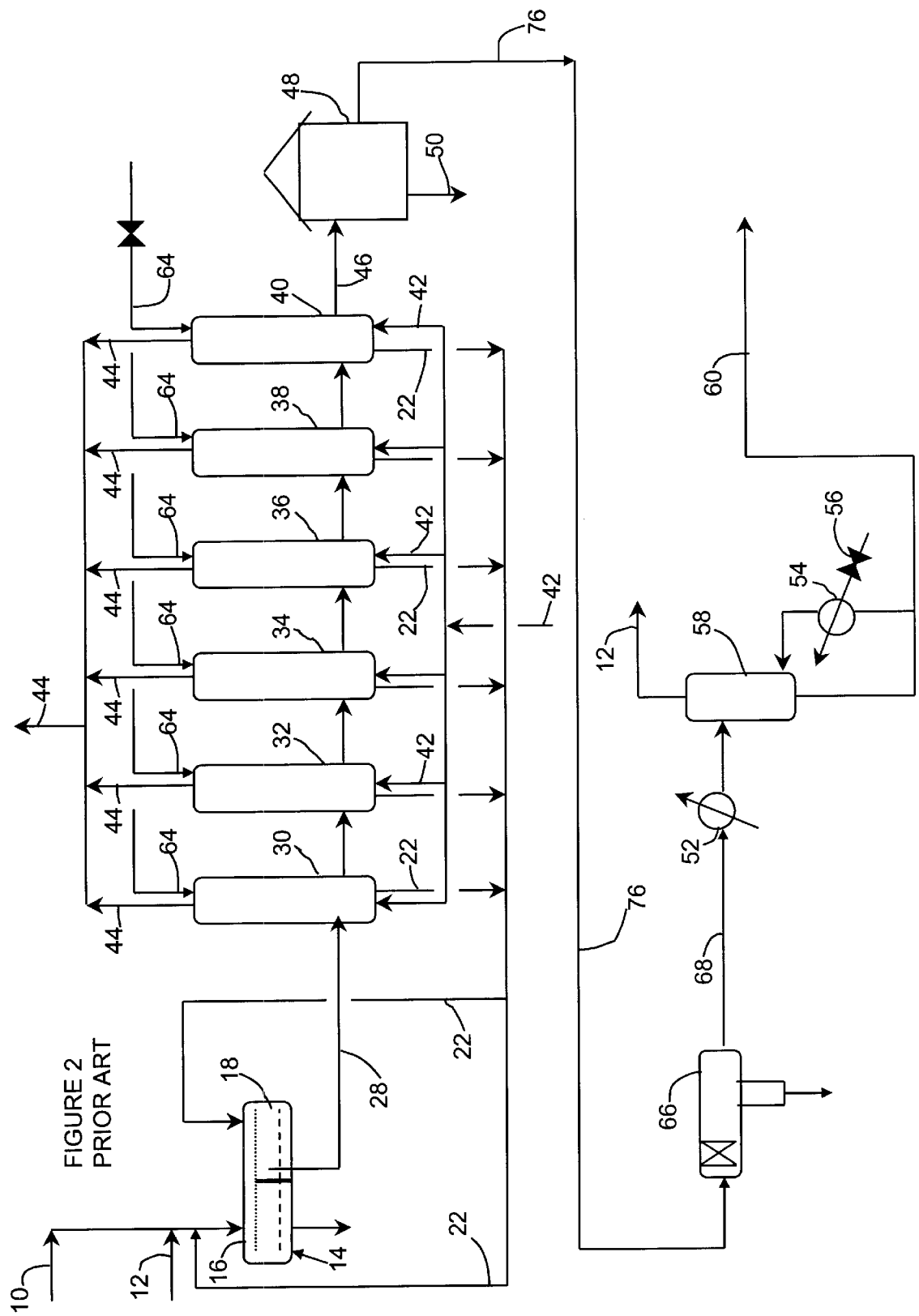
FIG. 2 is a schematic flow diagram illustrating a prior art embodiment of a method and system for manufacturing cumene hydroperoxide using alkali and alkaline earth metal salts or bases.

A 45 day controlled experimental trial was conducted in a continuous commercial cumene-to-phenol wet oxidation facility as shown in FIG. 2, using a combination of $Na_2CO_3$ and ammonia as the neutralizing agent. Process data and analytical measurements were collected daily in order to monitor the progress of the trial over time. Fresh cumene 10 was fed at a rate of 121,000 pounds per hour (lbs/hour) into a settler vessel where it was mixed with recycle streams of cumene 12. The resulting total organic flow 28 was fed into a six-reactor train 30, 32, 34, 36, 38, 40 at a rate of 563,000 lbs/hr. Raw material air 42 was continuously fed into the base of each of the six reactors at the following respective rates: 36,000, 30,000, 32,000, 29,000, 26,000, and 21,000 lbs/hr. The reaction pressure was held at 80 pounds per square inch (psig) in all of the reactors. The temperature maintained in the six series reactors was respectively: 225° F., 215° F., 210° F., 205° F., 200° F., and 195° F. The steady-state weight percent CHP concentrations were maintained inside the six reactors at near 6.0, 11.0, 15.5, 20.0, 24.0, 27.0 wt. % concentrations respectively.

Fresh $Na_2CO_3$ (10 wt. % in aqueous solution) 64 was continuously added to the top of each of the oxidation reactors in the following respective amounts: 260, 209, 203, 200, 189, 181 lbs/hr. The precision of the individual aqueous $Na_2CO_3$ flows was measured in advance of the trial run and determined to be +/−1.5 lb/hr. The resultant aqueous phase was drawn off the bottom of each of the reactors and the combined stream 22 sent to the settler vessel 14. A portion of the aqueous stream collected in the settler vessel was recycled into the tops of each of the reactors in the following respective amounts: 17500, 12500, 7500, 4000, 4000, 4000 lbs/hr.

44 lbs/hr of anhydrous ammonia was diluted with water to provide 0.5 wt. % $NH_4OH$/and continuously added to settler vessel. The precision of the ammonia flow was measured and determined to be +/−0.5 lb/hr. Inside the settler vessel the ammonia mixed with the two oxidate phases, partitioned primarily into the bottom aqueous phase in the settler vessel, and was subsequently fed forward in the recycled aqueous phase to the top of each of the reactors where both the ammonia and mixed alkali-salts entered the individual reactors. Oxidate samples were collected from each of the reactors for measurement of pH and formic acid and acetic acid content in parts per million (ppm). The organic acids and their respective salts were analyzed using an ion-exclusion chromatography technique.

The 27 wt. % CHP stream 46 emitted from the final reactor represents the final cumene-CHP oxidate product. It was continuously transferred to a tank 48 for surge and, after settling, was analyzed and its CHP molar selectivity was measured and calculated as a percentage. The cumene-CHP oxidate product 76 was then pumped continuously downstream at a rate of 584,000 lbs/hr for further processing at a coalescer vessel 66 and series of three distillation columns 58.

The 27 wt. % CHP oxidate was also analyzed by atomic absorption technique for sodium contamination. The coalescer oxidate effluent 68 was continuously fed forward from the coalescer 66 at a rate of 584,000 lbs/hr to the three distillation columns 58 at a rate of 584,000 lbs/hr. Steam heat was provided to the heat exchangers, which were carefully cleaned prior to the beginning of the trial run. At the distillation columns most of the cumene present was vaporized, removed overhead by vacuum distillation, and recycled to the settler vessel.

The steam supply to the primary reboiler 54 was controlled by a control valve 56 to maintain the desired temperatures in the distillation columns 58 and provide a final bottom concentrate of 82 wt. % CHP 60. As the reboiler heat exchanger 54 became fouled with salt over time it became necessary to open the steam supply valve 56 progressively more to overcome the negative effect of the reduced heat transfer due to the salt buildup on the heat exchanger tubes. The position of the steam supply valve (% open) was monitored and used as a good quantitative indicator of the progressive build up of the salt on the heat exchanger tubes as the salt build up fouled the heat exchanger. The final 82 wt. % CHP product 60 was then pumped at a rate of 182,000 lbs/hr to a downstream CHP acid cleavage reaction step where phenol and acetone are produced from the CHP.

The process performance data obtained from the above 45-day continuous experiment using the dual base addition process (ammonia plus sodium carbonate) is summarized below in Table 1.

TABLE 1

| | Reactors | | Product Stream | | |
|---|---|---|---|---|---|
| Day No. | Daily pH Variation | Formic Acid, ppm | CHP, wt. % | CHP Selectivity, % | Phenol, ppm |
| 1 | 6–8 | 1100 | 27 | 92.4 | 65 |
| 5 | 5–9 | 920 | 27.5 | 92.8 | 45 |
| 10 | 6–8 | 810 | 27.5 | 92.6 | 45 |
| 20 | 5–8 | 990 | 26.8 | 93 | 50 |
| 30 | 5–7 | 1060 | 27.5 | 92.2 | 60 |
| 40 | 6–8 | 950 | 26.7 | 92.6 | 60 |
| 50 | 6–9 | 860 | 27.2 | 92.5 | 65 |

The above data show wide pH swings occurring frequently within the reactors. This is likely due to free ammonia not being available for dissolution, due to mixed salt formation. This resulted in incomplete removal of formic acid and negatively impacted the CHP overall selectivity.

During the 45-day trial run, process data was simultaneously collected on the downstream section of the plant. The obtained data on entrained sodium in various streams and its accumulated impact on the reboiler and associated steam supply valve is shown below in Table 2.

TABLE 2

| Day No. | Sodium, ppm Stream No. 76, 68, 60 | Reboiler Valve 56, % open |
|---|---|---|
| 1 | 40/2/3 | 27 |
| 10 | 85/3/3 | 30 |
| 20 | 62/4/3 | 40 |
| 30 | 55/5/4 | 55 |
| 40 | 60/5/5 | 74 |
| 45 | 55/6/5 | 77 |

The above results demonstrate that the coalescer was unable to remove all of the entrained sodium salt and that the reboiler became progressively fouled as the accumulation of sodium salt deposits increased during the 45 day trial period.

Example 2

A second trial was conducted for a 26 day period using the same wet cumene oxidation process and conditions used in Example 1, except that ammonia was employed as the sole alkaline treating agent. As before, 44 lbs/hr of anhydrous ammonia was added as 0.5 wt. % ammonium hydroxide solution to the settler vessel. The reboiler was thoroughly cleaned prior to beginning the test run.

Process performance and analytical data was collected daily and are summarized below in Table 3:

TABLE 3

| | Reactors | | Product Stream | | |
|---|---|---|---|---|---|
| Day No. | Daily pH Variation | Formic Acid, ppm | CHP, wt. % | CHP Selectivity, % | Phenol, ppm |
| 1 | 7–8 | 220 | 28 | 93.5 | 25 |
| 5 | 7–9 | 180 | 27.5 | 92.8 | 28 |
| 15 | 7–8 | 310 | 27 | 93.4 | 35 |
| 26 | 7–9 | 290 | 27.8 | 93.6 | 35 |

The results show that the pH of the reaction is more closely controlled, organic acids more effectively neutralized, and phenol formation is reduced which is beneficial for CHP yields (selectivity).

Since no alkali-salt agents were added to the system during this 26-day trial run, no sodium contamination was expected in the downstream process streams and no negative impact on reboiler performance due to fouling was expected. Table 4 summarizes the data collected daily for confirmation of these expectations.

TABLE 4

| Day No. | Sodium, ppm Stream No 76, 68, 60 | Reboiler Valve 56, % open |
|---|---|---|
| 1 | 1/1/1 | 25 |
| 10 | 1/0/0 | 25 |
| 26 | 0/0/0 | 25 |

As shown by the above data, the position of the steam supply valve for the reboiler was unchanged during the 26-day trial run period, indicating no salt deposits or fouling of any kind.

Example 3

A third plant trial run was conducted for a 40 day period using the same conditions as in Example 2, except that only 24 lbs/hr of anhydrous ammonia was added as a 0.5 wt. % ammonia solution to the settler vessel. No other alkaline agents were employed. Table 5 summarizes the data collected daily during the 40-day period.

TABLE 5

| | Reactors | Product Stream | | |
|---|---|---|---|---|
| Day No. | Daily pH Variation | Formic Acid, ppm | CHP, wt. % | CHP Selectivity, % |
| 1 | 5–6 | 390 | 28 | 93 |
| 20 | 6–7 | 330 | 27.7 | 92.6 |
| 40 | 5–6 | 405 | 27.6 | 93.1 |

Also during this 40 day trial the downstream measurement of sodium was continued daily. Table 6 summarizes the data collected daily during the 40-day period.

TABLE 6

| Day No. | Sodium, ppm Stream No. 76, 68, 60 | Reboiler Valve 56, % open |
|---|---|---|
| 1 | 0/0/0 | 28 |
| 20 | 0/0/0 | 28 |
| 40 | 0/0/0 | 28 |

This data reinforces the results of Example 2 indicating that very low amounts of ammonia can be effectively and beneficially used as the sole neutralizing agent in a wet cumene oxidation process.

The method and system for manufacturing cumene hydroperoxide using free ammonia in a wet oxidation process with concurrent elimination of alkali and alkaline salt or base additives possesses several advantages over conventional processes, including the option to use wet oxidation, elimination of multiple neutralization agents, improved pH control, reduced phenol inhibitor formation, lower initial plant investment, higher plant on-stream factor, increased production rate, and elimination of complex systems and expensive equipment.

In particular, the free ammonia method may be conducted using the preferred safety "wet oxidation mode". The heterogeneous wet oxidation method is preferred over the alternative dry cumene oxidation method as the presence of a separate water phase inside the oxidation reactors provides enhanced cooling of the reaction via its evaporation, thus giving improved heat removal of the exothermic heat of reaction, and a more precise reactor temperature control. Also, the wet oxidation process requires less investment due to the use of less costly materials of construction.

The free ammonia method also does not employ troublesome alkali-metal salt additives. There are accordingly none of the immiscible, insoluble organic and alkaline phases, slowed mass transfer and lower degree of mixing between such phases, fouling of equipment due to salt deposits, or fluctuation of pH, each of which may require complex systems to overcome. The inventive method thus eliminates the need for complex systems and expensive equipment, and requires a lower initial plant investment, as there is no requirement for special equipment such as static mixers, counter-current extractors or coalescer units. The inventive process also employs a smaller quantity of ammonia as a neutralizing agent, which eliminates the need for periodic cleaning and plant shut downs associated with alkali and alkaline earth metal additives. Ammonia also acts as a single agent and is continuously available to neutralize acid inhibitors, and prevent phenol formation throughout the wet cumene oxidation process. Even though ammonia is not dibasic in nature and possesses no "inherent" buffering properties, the pH can be controlled more effectively, i.e., a tighter pH range is established, using ammonia than alkali-metal salt additives.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for manufacturing cumene hydroperoxide, comprising reacting cumene and oxygen in the presence of a water phase comprising aqueous ammonia, and in the absence of an additive comprising an alkali or alkaline earth metal, to form cumene hydroperoxide.

2. The method of claim 1, wherein the additive is selected from the group consisting of a Group IA or IIA metal salt, a Group IA or IIA metal carbonate, a Group IA or IIA metal phosphate, a Group IA or IIA metal hydroxide, and a Group IA or IIA metal hydrate.

3. The method of claim 1, wherein the cumene further comprises recycled cumene oxidate, recycled aqueous ammonia, or both.

4. The method of claim 1, wherein the ammonia is present in an amount effective to neutralize acids during the manufacture of the cumene hydroperoxide.

5. The method of claim 1, wherein the oxygen is provided in an air stream.

6. The method of claim 1, wherein the reacting comprises heating the cumene and the ammonia at a temperature of about 180 to about 220° F. at a pressure of about 70 to about 100 pounds per square inch gauge to the reaction mixture.

7. The method of claim 1, wherein the ammonia is present in an amount effective to maintain the pH of the reaction between about 5 and about 10.

8. The method of claim 1, wherein the ammonia is present in an amount effective to maintain the pH of the reaction between about 6 and about 9.

9. The method of claim 1, wherein the ammonia is present in an amount effective to maintain the pH of the reaction between about 7 and about 8.

10. A method for manufacturing cumene hydroperoxide, comprising reacting cumene and oxygen in the presence of an amount of aqueous ammonia effective to maintain the pH of the reaction between about 5 and about 10, and in the absence of an additive comprising an alkali or alkaline earth metal, to form cumene hydroperoxide, wherein the reacting comprises heating the cumene and the aqueous ammonia at a temperature of about 180 to about 220° F. at a pressure of about 70 to about 100 pounds per square inch gauge to the reaction mixture.

11. The method of claim 10, wherein the ammonia is present in an amount effective to maintain the pH of the reaction between about 6 and about 9.

12. The method of claim 10, wherein the ammonia is present in an amount effective to maintain the pH of the reaction between about 7 and about 8.

13. A system for producing cumene hydroperoxide, comprising:
   means for reacting cumene with oxygen in the presence of ammonium hydroxide, and in the absence of an additive comprising an alkali metal or alkaline earth metal.

14. The system of claim 13 further comprising means for mixing recycled cumene oxidate, recycled ammonium hydroxide, or both with the cumene.

15. The system of claim 13 further comprising means for concentrating the cumene hydroperoxide.

* * * * *